(12) United States Patent
Noordvyk et al.

(10) Patent No.: US 9,202,007 B2
(45) Date of Patent: Dec. 1, 2015

(54) METHOD, APPARATUS AND COMPUTER PROGRAM PRODUCT FOR PROVIDING DOCUMENTATION AND/OR ANNOTATION CAPABILITIES FOR VOLUMETRIC DATA

(75) Inventors: Allan Noordvyk, Surrey (CA); Leonard Yan, Burnaby (CA); Cristian Stegaru, Burnaby (CA); Radu Catalin Bocirnea, New Westminster (CA); Monica Paul, Vancouver (CA); Gillian Lo, New Westminster (CA)

(73) Assignee: McKesson Financial Holdings, Hamilton (BM)

( * ) Notice: Subject to any disclaimer, the term of this patent is extended or adjusted under 35 U.S.C. 154(b) by 0 days.

(21) Appl. No.: 12/691,294

(22) Filed: Jan. 21, 2010

(65) Prior Publication Data

US 2011/0179094 A1 Jul. 21, 2011

(51) Int. Cl.
*G06F 17/30* (2006.01)
*G06F 19/00* (2011.01)

(52) U.S. Cl.
CPC .................................. *G06F 19/321* (2013.01)

(58) Field of Classification Search
USPC .......................................................... 707/706
See application file for complete search history.

(56) References Cited

U.S. PATENT DOCUMENTS

| 7,369,134 B2 * | 5/2008 | Collins et al. ................. 345/543 |
| 2002/0184325 A1 * | 12/2002 | Killcommons et al. ...... 709/206 |
| 2010/0083153 A1 * | 4/2010 | Jain et al. ....................... 715/765 |
| 2010/0195878 A1 * | 8/2010 | Vion et al. ..................... 382/128 |

* cited by examiner

*Primary Examiner* — Amresh Singh
(74) *Attorney, Agent, or Firm* — Alston & Bird LLP

(57) ABSTRACT

A method for providing documentation and/or annotation capabilities for volumetric data may include receiving an indication of user insertion of an annotation with respect to a particular presentation state of a planar view of volumetric data and generating a medical image such as a DICOM image corresponding to the particular presentation state and including the annotation in response to receipt of the indication. A corresponding computer program product and apparatus are also provided.

14 Claims, 4 Drawing Sheets

METHOD, APPARATUS AND COMPUTER PROGRAM PRODUCT FOR PROVIDING DOCUMENTATION AND/OR ANNOTATION CAPABILITIES FOR VOLUMETRIC DATA

TECHNOLOGICAL FIELD

Embodiments of the present invention relate generally to health care management solutions and, more particularly, relate to the provision of documentation and/or annotation capabilities for volumetric data studies.

BACKGROUND

Researchers are faced with complex challenges of integrating huge volumes of data obtained from a wide range of distributed and uncoordinated systems, and sharing images and data with multidisciplinary teams within and across institutions. Images typically go through a complex workflow that may involve needs for data to be aligned, registered, and integrated with data from other sources, then analyzed, manipulated, and rendered using in-house software or scripts written for specific environments. Files may be distributed over a range of machines and stored in ad-hoc directories. When research requires cooperation between groups, bottlenecks can occur if specific personnel are unavailable to perform critical functions such as retrieving a file or generating a data set.

To improve capabilities with regard to handling such large volumes of data, clinical connectivity standards have been developed. For example, Digital Imaging and Communications in Medicine (DICOM), which is a standard file format and network communication protocol for handling, storing, printing, and transmitting information in medical imaging, has been developed as a tool for integrating devices across diverse networks and institutions with respect to handling medical images. Using DICOM and other generic file formats, the development of a picture archiving and communication system (PACS) that can integrate diverse devices has been made a reality. Accordingly, the ability to generate and share medical images has been greatly enhanced, thereby also enhancing the ability of medical researchers and practitioners to utilize their skills to advance research and treat patients.

However, although it is much easier to share volumetric data that can be opened by any number of other authorized parties, the actual manipulation of the data can still sometimes be unwieldy in certain cases. For example, when a user (e.g., a radiologist) is studying volumetric data and creates an annotation to the data in a particular presentation state, it may be very difficult for the user to later find the same view previously presented or even to locate the annotation. Accordingly, it may be desirable to provide methods, apparatuses, computer program products, and systems for providing documentation and/or annotation capabilities for volumetric data studies.

BRIEF SUMMARY

A method, apparatus and system are therefore provided to enable the provision documentation and/or annotation capabilities for volumetric data studies that may address some of the problems discussed above. Accordingly, for example, medical images (e.g., DICOM images) may be automatically generated when annotations are made and, in some cases, bookmarked to enable easy retrieval of such images at a later time.

In one exemplary embodiment, a method for providing documentation and/or annotation capabilities for volumetric data studies is provided. The method may include receiving an indication of user insertion of an annotation with respect to a particular presentation state of a planar view of volumetric data and generating (e.g., via processing circuitry) a medical image (e.g., a DICOM image) corresponding to the particular presentation state and including the annotation in response to receipt of the indication.

In another exemplary embodiment, a computer program product for providing documentation and/or annotation capabilities for volumetric data studies is provided. The computer program product may include at least one computer-readable storage medium having computer-executable program code instructions stored therein. The computer-executable program code instructions may include program code instructions for receiving an indication of user insertion of an annotation with respect to a particular presentation state of a planar view of volumetric data and generating a medical image (e.g., a DICOM image) corresponding to the particular presentation state and including the annotation in response to receipt of the indication.

In another exemplary embodiment, an apparatus for providing documentation and/or annotation capabilities for volumetric data studies is provided. The apparatus may include processing circuitry. The processing circuitry may be configured for receiving an indication of user insertion of an annotation with respect to a particular presentation state of a planar view of volumetric data and generating a medical image (e.g., a DICOM image) corresponding to the particular presentation state and including the annotation in response to receipt of the indication.

BRIEF DESCRIPTION OF THE SEVERAL VIEWS OF THE DRAWING(S)

Having thus described embodiments of the invention in general terms, reference will now be made to the accompanying drawings, which are not necessarily drawn to scale, and wherein:

Figure 3:
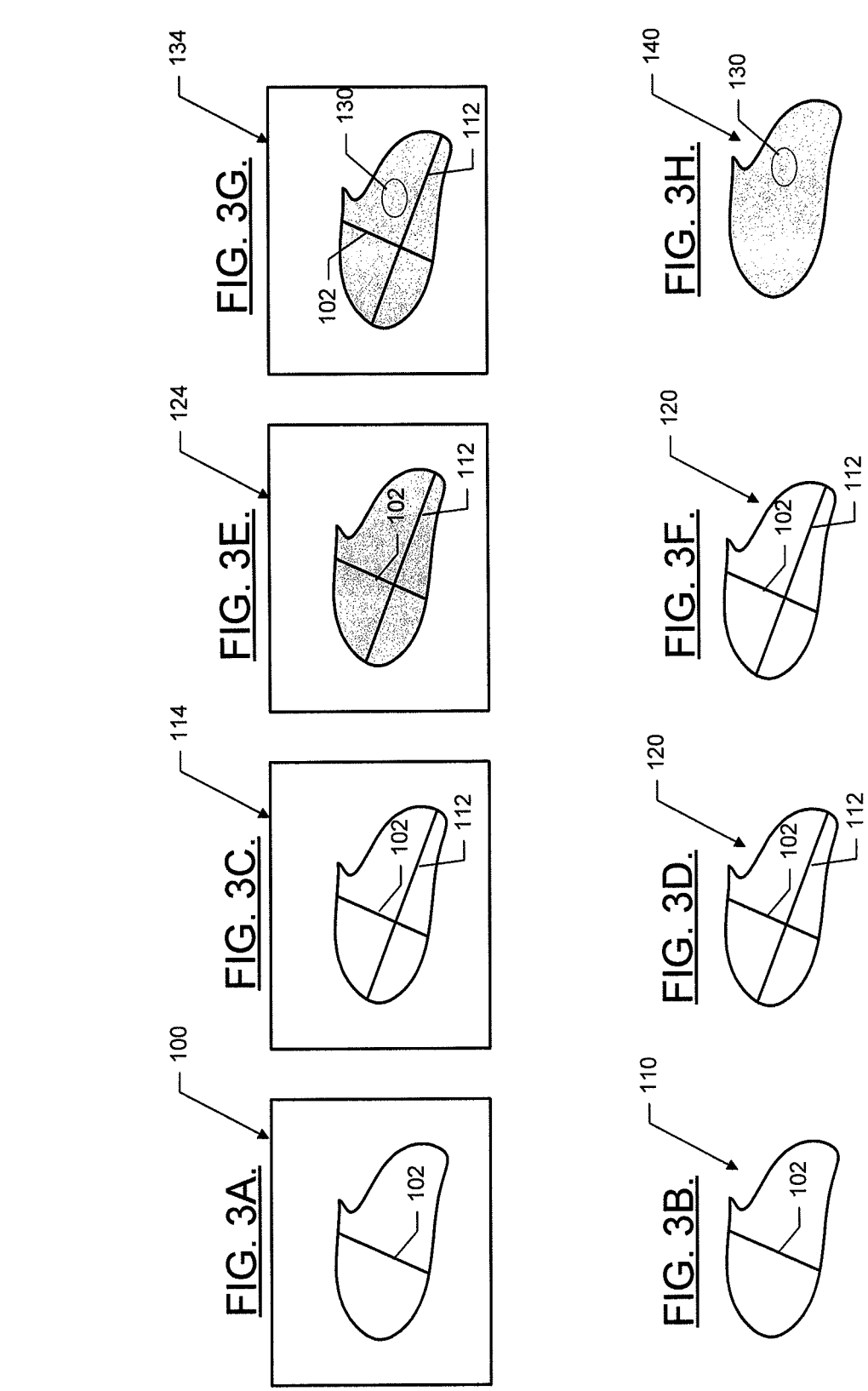
Figure 4:
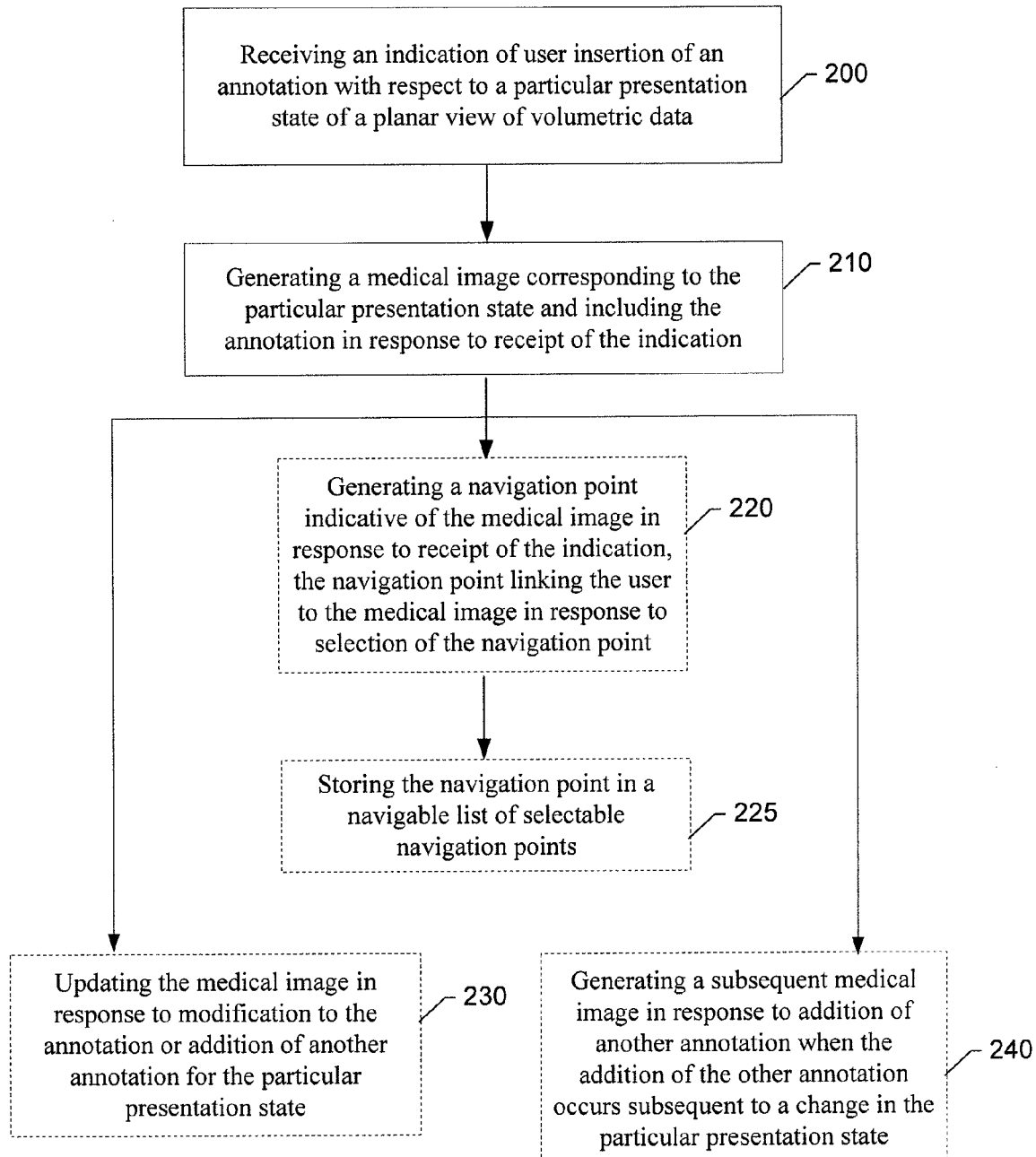

FIG. 3, which includes FIGS. 3A to 3H, shows a series of navigation and corresponding image generation operations according to an example embodiment of the present invention; and FIG. 4 is a block diagram according to an exemplary method for providing documentation and/or annotation capabilities for volumetric data studies according to an exemplary embodiment of the present invention.

DETAILED DESCRIPTION

Embodiments of the present invention will now be described more fully hereinafter with reference to the accompanying drawings, in which some, but not all embodiments of the invention are shown. Indeed, embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As indicated above, embodiments of the present invention are aimed at providing a mechanism by to improve documentation and/or annotation capabilities for review of volumetric data studies. In some embodiments, in response to the insertion of an annotation into data of a volumetric study, a medical image (e.g., a DICOM image) may be generated automatically. However, beyond merely creating an image, the presentation state that existed during insertion of the annotation may also be saved. In some embodiments, a tag or bookmark may also be provided for the generated medical image so that the image may be retrieved more easily at a later time. Accordingly, by retrieving an image associated with a particular tag or bookmark, the user may retrieve the automatically generated image with the corresponding annotation and in the same presentation state in which the annotation was created.

Figure 1:
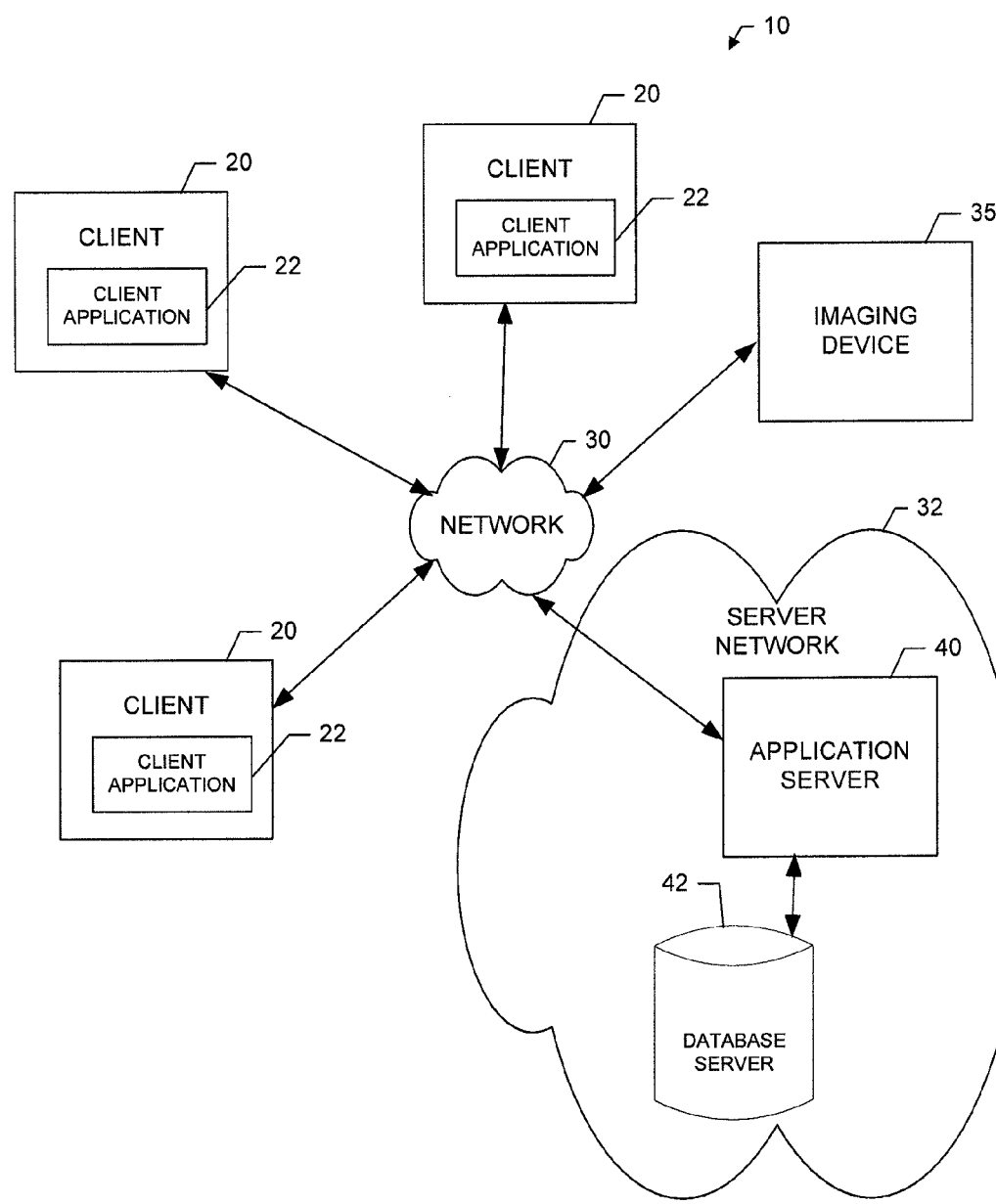
FIG. 1 is a block diagram illustrating a system for providing documentation and/or annotation capabilities for volumetric data studies according to an exemplary embodiment of the present invention.

An exemplary embodiment of the invention will now be described in reference to FIG. 1, which illustrates an exemplary system in which an embodiment of the present invention may be employed. As shown in FIG. 1, a system according to an exemplary embodiment may include one or more clients 20 that may, in some cases, be associated with different corresponding units or departments of a hospital or healthcare system. However, in other cases, the clients 20 could actually be associated with entirely different organizations or healthcare systems. For example, one client 20 may be associated with a first entity (e.g., a medical imaging unit) and a second client 20 may be associated with a second entity (e.g., a radiologist).

Each client 20 may be, for example, a computer (e.g., a personal computer, laptop computer, network access terminal, or the like) or may be another form of computing device (e.g., a personal digital assistant (PDA), cellular phone, or the like) capable of communication with a network 30. As such, for example, each client 20 may include (or otherwise have access to) memory for storing instructions or applications for the performance of various functions and a corresponding processor for executing stored instructions or applications. Each client 20 may also include software and/or corresponding hardware for enabling the performance of the respective functions of the clients as described below. In an exemplary embodiment, one or more of the clients 20 may include a client application 22 configured to operate in accordance with an exemplary embodiment of the present invention. In this regard, for example, the client application 22 may include software for enabling a respective one of the clients 20 to communicate with the network 30 for the provision of and receipt of information associated with providing documentation and/or annotation of volumetric data. As such, for example, the client application 22 may include corresponding executable instructions for configuring the client 20 to provide corresponding functionalities for the provision of and receipt of information associated with retrieval of medical imaging data (e.g., a volumetric data study) stored in a standard format that may be available locally or via the network 30. The client application 22 may also include corresponding executable instructions for configuring the client 20 to provide corresponding functionalities for the documentation and/or annotation of volumetric data as described in greater detail below.

The network 30 may be a data network, such as a local area network (LAN), a metropolitan area network (MAN), a wide area network (WAN) (e.g., the Internet), and/or the like, which may couple the clients 20 to devices such as processing elements (e.g., personal computers, server computers or the like) or databases. Communication between the network 30, the clients 20 and the devices or databases (e.g., servers) to which the clients 20 are coupled may be accomplished by either wireline or wireless communication mechanisms and corresponding protocols. In some embodiments, the network 30 may be a secured network to enable secure transmission of patient information in accordance with privacy standards.

The network 30 may also be in communication with an imaging device 35 (or multiple imaging devices). The imaging device 35 may be configured to provide medical images according to one or more different imaging modalities such as, for example, magnetic resonance imaging (MRI), computed tomography (CT) or numerous other imaging modalities. The medical images may be stored thereafter as a study associated with a particular patient in a server network (e.g. server network 32) via the network 30.

In an exemplary embodiment, one of the devices to which the clients 20 may be coupled via the network 30 may include one or more application servers (e.g., application server 40), and/or a database server 42, which together may form respective elements of a server network 32. Although the application server 40 and the database server 42 are each referred to as "servers", this does not necessarily imply that they are embodied on separate servers or devices. As such, for example, a single server or device may include both entities and the database server 42 could merely be represented by a database or group of databases physically located on the same server as the application server 40. The application server 40 and the database server 42 may each include hardware and/or software for configuring the application server 40 and the database server 42, respectively, to perform various functions. As such, for example, the application server 40 may include processing logic and memory enabling the application server 40 to access and/or execute stored computer readable instructions for performing various functions. In an exemplary embodiment, one function that may be provided by the application server 40 may be the provision of documentation and/or annotation services with respect to medical images to the clients 20. As such, in various exemplary embodiments, operations and functionalities described herein in relation to documentation and/or annotation of volumetric data may be fully implemented at one device, or may be implemented in a distributed fashion with different activities being shared between the client 20 and the application server 40. Thus, the application server 40 may include a service application comprising stored instructions for accessing information and providing such information to the client applications 22 based on requests provided at each respective client 20.

Additionally or alternatively, the application server 40 may be configured to enable the clients 20 to provide information to and/or retrieve information from the application server 40, for use by the client application 22 and/or the application server 40 in producing, maintaining and/or supplying study data such as volumetric data and medical images (e.g., DICOM images) for a particular patient. In an example embodiment, the application server 40 (or servers) may include particular applications related to various different medical imaging standards to enable users at various clients 20 to retrieve data and manipulate the data to review and study the data in connection with practicing example embodiments of the present invention. In some examples, the studies generated by the imaging device 35 may be stored on the database server 42 and accessible by the clients 20 via the application server 40 for the performance of functionalities in accordance with exemplary embodiments of the present invention.

Figure 2:
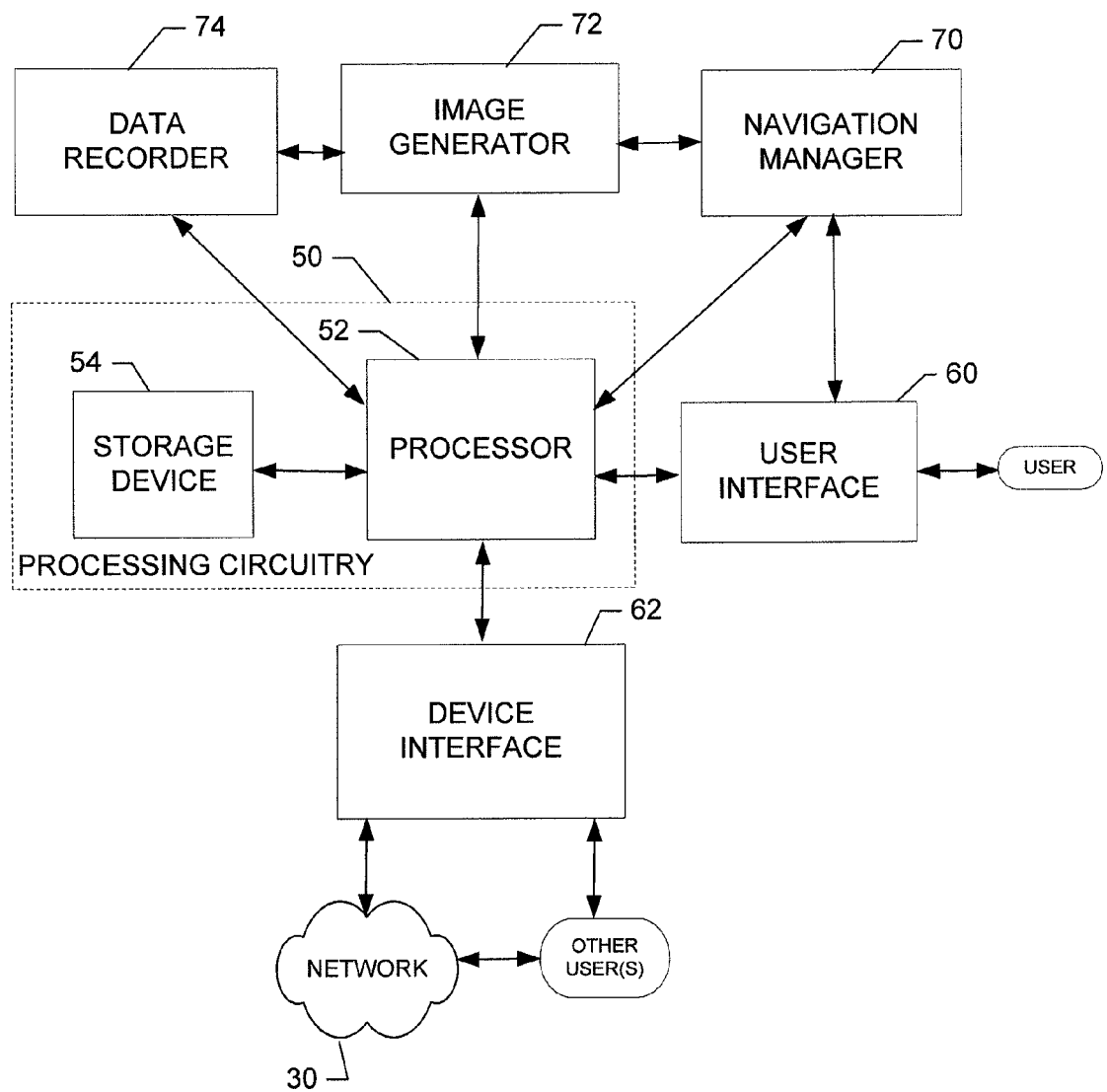
FIG. 2 is a block diagram showing various components that may be included in an apparatus for providing documentation and/or annotation capabilities for volumetric data studies according to an exemplary embodiment of the present invention.

An exemplary embodiment of the invention will now be described with reference to FIG. 2. FIG. 2 shows certain elements of an apparatus for providing documentation and/or annotation capabilities for volumetric data studies according to an exemplary embodiment. The apparatus of FIG. 2 may be employed, for example, on a client (e.g., any of the clients 20 of FIG. 1) or a variety of other devices (such as, for example, a network device, server, proxy, or the like (e.g., the application server 40 of FIG. 1)). Alternatively, embodiments may be employed on a combination of devices. Accordingly, some embodiments of the present invention may be embodied wholly at a single device (e.g., the application server 40) or by devices in a client/server relationship (e.g., the application server 40 and one or more clients 20). Furthermore, it should be noted that the devices or elements described below may not be mandatory and thus some may be omitted in certain embodiments.

Referring now to FIG. 2, an apparatus for providing documentation and/or annotation capabilities for volumetric data studies is provided. The apparatus may include or otherwise be in communication with processing circuitry 50 that is configured to perform data processing, application execution and other processing and management services according to an exemplary embodiment of the present invention. In one embodiment, the processing circuitry 50 may include a processor 52, a storage device 54 that may be in communication with or otherwise control a user interface 60 and a device interface 62. As such, the processing circuitry 50 may be embodied as a circuit chip (e.g., an integrated circuit chip) configured (e.g., with hardware, software or a combination of hardware and software) to perform operations described herein. However, in some embodiments, the processing circuitry 50 may be embodied as a portion of a server, computer, laptop, workstation or even one of various mobile computing devices. In situations where the processing circuitry 50 is embodied as a server or at a remotely located computing device, the user interface 60 may be disposed at another device (e.g., at a computer terminal or client device such as one of the clients 22) that may be in communication with the processing circuitry 50 via the device interface 62 and/or a network (e.g., network 30).

The user interface 60 may be in communication with the processing circuitry 50 to receive an indication of a user input at the user interface 60 and/or to provide an audible, visual, mechanical or other output to the user. As such, the user interface 60 may include, for example, a keyboard, a mouse, a joystick, a display, a touch screen, a microphone, a speaker, a cell phone, or other input/output mechanisms. In an exemplary embodiment, the user interface 60 may include interface options for changing presentation state parameters for a current view of a particular two dimensional image (e.g., a slice of data representing a planar view of a portion of the three dimensional volumetric data) in an opened study in order to manipulate the image to obtain a different view. The user interface 60 may also provide options to the user for providing annotations to a current view.

The device interface 62 may include one or more interface mechanisms for enabling communication with other devices and/or networks. In some cases, the device interface 62 may be any means such as a device or circuitry embodied in either hardware, software, or a combination of hardware and software that is configured to receive and/or transmit data from/to a network and/or any other device or module in communication with the processing circuitry 50. In this regard, the device interface 62 may include, for example, an antenna (or multiple antennas) and supporting hardware and/or software for enabling communications with a wireless communication network and/or a communication modem or other hardware/software for supporting communication via cable, digital subscriber line (DSL), universal serial bus (USB), Ethernet or other methods. In situations where the device interface 62 communicates with a network, the network may be any of various examples of wireless or wired communication networks such as, for example, data networks like a Local Area Network (LAN), a Metropolitan Area Network (MAN), and/or a Wide Area Network (WAN), such as the Internet.

In an exemplary embodiment, the storage device 54 may include one or more memory devices such as, for example, volatile and/or non-volatile memory that may be either fixed or removable. The storage device 54 may be configured to store information, data, applications, instructions or the like for enabling the apparatus to carry out various functions in accordance with exemplary embodiments of the present invention. For example, the storage device 54 could be configured to buffer input data for processing by the processor 52. Additionally or alternatively, the storage device 54 could be configured to store instructions for execution by the processor 52. As yet another alternative, the storage device 54 may include one of a plurality of databases (e.g., database server 42) that may store a variety of files, contents or data sets. Among the contents of the storage device 54, applications (e.g., client application 22 or a service application) may be stored for execution by the processor 52 in order to carry out the functionality associated with each respective application.

The processor 52 may be embodied in a number of different ways. For example, the processor 52 may be embodied as various processing means such as a microprocessor or other processing element, a coprocessor, a controller or various other computing or processing devices including integrated circuits such as, for example, an ASIC (application specific integrated circuit), an FPGA (field programmable gate array), a hardware accelerator, or the like. In an exemplary embodiment, the processor 52 may be configured to execute instructions stored in the storage device 54 or otherwise accessible to the processor 52. As such, whether configured by hardware or software methods, or by a combination thereof, the processor 52 may represent an entity (e.g., physically embodied in circuitry) capable of performing operations according to embodiments of the present invention while configured accordingly. Thus, for example, when the processor 52 is embodied as an ASIC, FPGA or the like, the processor 52 may be specifically configured hardware for conducting the operations described herein. Alternatively, as another example, when the processor 52 is embodied as an executor of software instructions, the instructions may specifically configure the processor 52 to perform the operations described herein.

In an exemplary embodiment, the processor 52 (or the processing circuitry 50) may be embodied as, include or otherwise control navigation manager 70, an image generator 72, and a data recorder 74. The navigation manager 70, the image generator 72, and the data recorder 74 may each be any means such as a device or circuitry operating in accordance with software or otherwise embodied in hardware or a combination of hardware and software (e.g., processor 52 operating under software control, the processor 52 embodied as an ASIC or FPGA specifically configured to perform the operations described herein, or a combination thereof) thereby configuring the device or circuitry to perform the corresponding functions of the navigation manager 70, the image generator 72, and the data recorder 74, respectively, as described below.

The navigation manager 70 may be configured to enable a user to navigate through a volume that has been imaged. Thus, for example, the navigation manager 70 may receive indications of user commands from the user interface 60 and may manipulate views of volumetric data to be presented to the user (e.g., via a display of the user interface 60) according to the commands received. In an exemplary embodiment, the navigation manager 70 may be configured to enable users to modify such presentation state parameters as, for example, plane position and orientation, zoom factor, pan factor, window/level, slab thickness, projection type, and/or the like. Accordingly, the navigation manager 70 may enable the user to navigate through a three dimensional volume to alter the orientation and boundaries for various two dimensional planar views of slices of the volume in order to enable study of the respective two dimensional planar views by the user.

In an example embodiment, the navigation manager 70 may also enable the user to provide annotations to the volumetric data. Thus, for example, the user may be enabled to provide linear measurement annotations, circle features of interest, insert textual descriptors, insert flags or indicators, or provide other annotations using the navigation manager.

For conventional navigation and annotation procedures, the user would typically be required to manually navigate back through the volume to look for annotations that were previously entered by attempting to find the same presentation state in which the annotation was entered. This could be a time consuming and difficult task. Accordingly, embodiments of the present invention may enable users to re-locate annotations in the same presentation state in which such annotations were entered in a relatively simple and rapid way via the image generator 72 and the data recorder 74. In this regard, the image generator 72 and the data recorder 74 may each be configured to operate in connection with the navigation manager 70 to automatically create medical images (e.g., DICOM images) and record information about the automatically generated images to enable relatively easy retrieval of such images at a later time.

The image generator 72 may be configured to automatically generate images. Moreover, the image generator 72 may be configured to operate responsive to a particular trigger, namely the insertion of an annotation in a three dimensional volume. As such, the image generator 72 may monitor or otherwise receive reports of activity of the navigation manager 70, at least with respect to annotation insertions. In response to receipt of an indication that an annotation has been placed in the volume, the image generator 72 captures a medical image (e.g., a DICOM image) representing the plane on which the annotation was placed within the volume. The medical image, which is a two dimensional image, is captured to share the same presentation state of the three dimensional plane at the point of capture. A two dimensional representation of the annotation may also be placed on the volume and on the generated image. Thus, for example, the provision of an annotation within a volume automatically causes a capture of a DICOM image having the presentation state existing when the annotation was provided, and the annotation itself is also recorded on the image. DICOM images may also be captured if the user flags the volume.

The data recorder 74 may store the medical image generated (e.g., in the database server 42 and/or the storage device 54) to enable retrieval or archiving of the medical image in association with the volume and therefore in association with the corresponding patient. Thus, essentially the same image viewed by the user when the annotation was created is preserved in the corresponding same presentation state so that the view provided when the annotation was created, and the annotation itself, may both be viewed at a later time. Attributes preserved by the medical image may include, but not be limited to, the source volume for the currently displayed plane, plane position and orientation (e.g., for multi-planar reformatted (MPR) view), zoom factor, pan position, window/level, slab thickness, projection type, persistent annotations, and/or the like.

In response to a user update of an annotation, the corresponding annotation on the medical image may also be updated. For example, if the user modifies the font, color, position, shape, etc., of the annotation, the annotation on the stored medical image may also be updated. Thus, it may not be necessary to provide a new image for simple annotation updates.

Each medical image generated by the image generator 72 may have a unique association with the three dimensional plane to which it corresponds. In this regard, for example, the unique association between a three dimensional plane and a corresponding DICOM image may be defined by properties including the source volume for the currently displayed plane, the plane position and orientation, pan position, window/level, slab thickness and projection type. In an exemplary embodiment, the image generator 72 may create a new medical image in response to any one of the above listed properties experiencing a value change. Thus, for example, if a set of presentation state parameters define a particular view and a first annotation is placed thereon, the image generator 72 may generate a first DICOM image having the first annotation. If a second annotation is inserted without changing any of the presentation state parameters, then the second annotation may be placed on the first DICOM image as well. However, if any presentation state parameter is changed prior to the second annotation being inserted, then a second DICOM image may be generated with the second annotation recorded thereon. FIG. 3 illustrates an example following the scenario.

In this regard, FIG. 3, which includes FIGS. 3A to 3H, shows a series of navigation and corresponding image generation operations according to an example embodiment. FIG. 3A shows an image 100 in an MPR view with an annotation 102 inserted thereon. FIG. 3B shows a corresponding medical image 110 generated by the image generator 72 for storage by the data recorder 74. The medical image 110 represents a first derived view including the annotation 102 and has the same presentation state parameters as the image 100 of FIG. 3A. In FIG. 3C, the user adds a second annotation 112 to an image 114 on the same MPR plane with the same presentation. Since the presentation parameters are the same, the corresponding medical image 120 of FIG. 3D is updated to associate the second annotation 112 with the first derived view. In FIG. 3E, the user stays on the same MPR plane, but changes the presentation (as indicated by the shading in image 124). As shown in FIG. 3F, although the presentation state has changed, there has been no annotation trigger to cause another medical image to be generated so the first derived view is unchanged and the medical image of FIG. 3F is the same as the medical image 120 of FIG. 3D. In FIG. 3G, the user has added a third annotation 130 to image 124. Since the addition of the third annotation 130 has been added subsequent to a presentation state change, the first derived view is not updated. Instead, the addition of the third annotation 130 triggers the generation of a second derived view with the new presentation state parameters and the annotation added since the presentation state parameters were changed. Accordingly, FIG. 3H shows the second derived view for a medical image 140 created according to the presentation state when the third annotation 130 was added and including the third annotation 130. Thus, the presentation state links the medical image to the volume in which the medical image was captured.

As indicated above, the data recorder 74 stores each of the medical images generated (or updated) by the image generator 72. However, in some embodiments, the data recorder 74 may further be configured to provide enablement for the user to navigate back to the location of a key finding (e.g., an annotation) in a volume being studied. Moreover, the user may be enabled to access key findings in the same presentation state in which such findings were initially created or updated. To provide this functionality, the data recorder 74 may be configured to generate navigation points (e.g., tags or bookmarks) in response to creation of annotations or modifications to annotations. In some cases, navigation points may also be created in response to the user flagging a plane in a volume. In an exemplary embodiment, the data recorder 74 may be configured to store the navigation points in the storage device 54 such that the navigation points may be retrieved in a current session or even in a subsequent session.

Accordingly, for example, when an annotation is added in some embodiments, the image generator 72 may create a medical image (e.g., a DICOM image) corresponding to the presentation state when the annotation is created and including the annotation. The data recorder 74 may then store the medical image and also generate and store a navigation point corresponding to the medical image. In an example embodiment, the navigation points may be accessible in a common location so that the user may, for example, view a list of navigation points and select one or more of the navigation points. In response to selection of a navigation point, the corresponding medical image associated therewith may be retrieved so that the user can view the corresponding medical image in the same presentation state that was present during creation of the annotation(s) that triggered creation of the medical image.

Embodiments of the present invention may therefore be practiced using an apparatus such as the one depicted in FIG. 2. However, other embodiments may be practiced in connection with a computer program product for performing embodiments of the present invention. FIG. 4 is a flowchart of a method and program product according to exemplary embodiments of the invention. Each block of the flowchart of FIG. 4, and combinations of blocks in the flowchart, may be implemented by various means, such as hardware, firmware, processor, circuitry and/or another device associated with execution of software including one or more computer program instructions. Thus, for example, one or more of the procedures described above may be embodied by computer program instructions, which may embody the procedures described above and may be stored by a storage device (e.g., storage device 54) and executed by processing circuitry (e.g., processor 52).

As will be appreciated, any such stored computer program instructions may be loaded onto a computer or other programmable apparatus (i.e., hardware) to produce a machine, such that the instructions which execute on the computer or other programmable apparatus implement the functions specified in the flowchart block(s). These computer program instructions may also be stored in a computer-readable medium comprising memory that may direct a computer or other programmable apparatus to function in a particular manner, such that the instructions stored in the computer-readable memory produce an article of manufacture including instructions to implement the function specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart block(s).

In this regard, a method according to one embodiment of the invention, as shown in FIG. 4, may include receiving an indication of user insertion of an annotation with respect to a particular presentation state of a planar view of volumetric data at operation 200 and generating (e.g., via processing circuitry) a medical image (e.g., a DICOM image) corresponding to the particular presentation state and including the annotation in response to receipt of the indication at operation 210.

In some cases, the method may include additional optional operations, an example of which is shown in dashed lines in FIG. 4. Additionally, in some cases, some of the operations described herein may be modified. In an exemplary embodiment, the method may further include generating a navigation point indicative of the medical image in response to receipt of the indication at operation 220. The navigation point may link the user to the medical image in response to selection of the navigation point. In some cases, the method may include storing the navigation point in a navigable list of selectable navigation points at operation 225. In an example embodiment, the method may further include updating the medical image in response to modification to the annotation or addition of another annotation for the particular presentation state at operation 230 and/or generating a subsequent medical image in response to addition of another annotation when the addition of the other annotation occurs subsequent to a change in the particular presentation state at operation 240. In some embodiments, generating the medical image may further include creating the medical image and storing the medical image created in a memory. Other modifications are also possible. The modifications and optional operations may be included in any combination and in any order with respect to the operations 200-240 described above.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method comprising:
   during navigation through a three-dimensional volume, receiving an indication of user insertion of a first annotation with respect to a particular presentation state of a planar view of volumetric data having at least three dimensions;
   including the first annotation in the three-dimensional volume defined by the volumetric data;
   generating from the volumetric data having at least three dimensions, via processing circuitry in response to the first annotation, a new two-dimensional medical image representing a plane on which the first annotation was inserted within the volumetric data, wherein the new two-dimensional medical image also corresponds to the particular presentation state of the volumetric data when the first annotation was inserted and includes the first annotation in response to receipt of the indication such that both the three-dimensional volume defined by the volumetric data and the new two-dimensional medical image that was generated include the first annotation, wherein the new two-dimensional medical image is distinct from the three-dimensional volume, and wherein generating the two-dimensional medical image comprises storing the medical image in a memory;

generating a navigation point associated with the first annotation in response to receipt of the indication of the first annotation, the navigation point linking the user to the particular presentation state in which the first annotation was inserted in response to selection of the navigation point;

receiving an indication of user insertion of a second annotation of the planar view of the volumetric data, wherein the planar view of the volumetric data is along a common plane as when the indication of the first annotation was received;

in an instance in which the presentation state of the planar view of the volumetric data when the indication of the second annotation was received is identical to the presentation state when the indication of the first annotation was received, updating the two-dimensional medical image to include both the first and second annotations; and in an instance in which the presentation state of the planar view of the volumetric data when the indication of the second annotation was received is different from the presentation state when the indication of the first annotation was received, generating another two-dimensional medical image that corresponds to the presentation state of the volumetric data when the second annotation was inserted and includes the second annotation.

2. The method of claim 1, wherein generating the medical image comprises generating a Digital Imaging and Communications in Medicine (DICOM) image.

3. The method of claim 1, wherein generating the medical image further comprises creating the medical image.

4. The method of claim 1, further comprising storing the navigation point in a navigable list of selectable navigation points.

5. The method of claim 1, further comprising updating the medical image in response to modification to the first annotation.

6. A computer program product comprising at least one computer-readable storage medium having computer-executable program code instructions stored therein, the computer-executable program code instructions comprising:

program code instructions for receiving, during navigation through a three-dimensional volume, an indication of user insertion of a first annotation with respect to a particular presentation state of a planar view of volumetric data having at least three dimensions;

program code instructions for including the first annotation in the three-dimensional volume defined by the volumetric data;

program code instructions for generating from the volumetric data having at least three dimensions, in response to the first annotation, a new two-dimensional medical image representing a plane on which the first annotation was inserted within the volumetric data, wherein the new two-dimensional medical image also corresponds to the particular presentation state of the volumetric data when the first annotation was inserted and includes the first annotation in response to receipt of the indication such that both the three-dimensional volume defined by the volumetric data and the new two-dimensional medical image that was generated include the first annotation, wherein the new two-dimensional medical image is distinct from the three-dimensional volume, and wherein the program code instructions for generating the two-dimensional medical image comprise program code instructions for storing the medical image in a memory;

program code instructions for generating a navigation point associated with the first annotation in response to receipt of the indication of the first annotation, the navigation point linking the user to the particular presentation state in which the first annotation was inserted in response to selection of the navigation point;

program code instructions for receiving an indication of user insertion of a second annotation of the planar view of the volumetric data, wherein the planar view of the volumetric data is along a common plane as when the indication of the first annotation was received;

program code instructions for updating, in an instance in which the presentation state of the planar view of the volumetric data when the indication of the second annotation was received is identical to the presentation state when the indication of the first annotation was received, the two-dimensional medical image to include both the first and second annotations; and program code instructions for generating, in an instance in which the presentation state of the planar view of the volumetric data when the indication of the second annotation was received is different from the presentation state when the indication of the first annotation was received, another two-dimensional medical image that corresponds to the presentation state of the volumetric data when the second annotation was inserted and includes the second annotation.

7. The computer program product of claim 6, wherein program code instructions for generating the medical image include instructions for generating a Digital Imaging and Communications in Medicine (DICOM) image.

8. The computer program product of claim 6, wherein program code instructions for generating the medical image further include instructions for creating the medical image.

9. The computer program product of claim 6, further comprising program code instructions for storing the navigation point in a navigable list of selectable navigation points.

10. The computer program product of claim 6, further comprising program code instructions for updating the medical image in response to modification to the first annotation.

11. An apparatus comprising processing circuitry configured to:

during navigation through a three-dimensional volume, receive an indication of user insertion of a first annotation with respect to a particular presentation state of a planar view of volumetric data having at least three dimensions;

include the annotation in the three-dimensional volume defined by the volumetric data;

in response to the first annotation, generate from the volumetric data having at least three dimensions a new two-dimensional medical image representing a plane on which the first annotation was inserted within the volumetric data, wherein the new two-dimensional medical image also corresponds to the particular presentation state of the volumetric data when the first annotation was inserted and includes the first annotation in response to receipt of the indication such that both the three-dimensional volume defined by the volumetric data and the new two-dimensional medical image that was generated include the first annotation, wherein the new two-dimensional medical image is distinct from the three-dimensional volume, and wherein generating the two-dimensional medical image comprises storing the medical image in a memory; and generate a navigation point associated with the first annotation in response to receipt of the indication of the first annotation, the navigation point linking the user to the particular presentation state in which the first annotation was inserted in response to selection of the navigation point;

receive an indication of user insertion of a second annotation of the planar view of the volumetric data, wherein the planar view of the volumetric data is along a common plane as when the indication of the first annotation was received;

in an instance in which the presentation state of the planar view of the volumetric data when the indication of the second annotation was received is identical to the presentation state when the indication of the first annotation was received, update the two-dimensional medical image to include both the first and second annotations; and in an instance in which the presentation state of the planar view of the volumetric data when the indication of the second annotation was received is different from the presentation state when the indication of the first annotation was received, generate another two-dimensional medical image that corresponds to the presentation state of the volumetric data when the second annotation was inserted and includes the second annotation.

12. The apparatus of claim 11, wherein the processing circuitry is configured to generate the medical image as a Digital Imaging and Communications in Medicine (DICOM) image.

13. The apparatus of claim 11, wherein the processing circuitry is further configured to store the navigation point in a navigable list of selectable navigation points.

14. The apparatus of claim 11, wherein the processing circuitry is further configured to update the medical image in response to modification to the first annotation.

* * * * *